United States Patent [19]

Kydonieus et al.

[11] Patent Number: 4,792,450

[45] Date of Patent: Dec. 20, 1988

[54] DEVICE FOR CONTROLLED RELEASE DRUG DELIVERY

[75] Inventors: Agis F. Kydonieus, Kendall Park, N.J.; Bret Berner, New York, N.Y.

[73] Assignee: Hercon Laboratories Corporation, South Plainfield, N.J.

[21] Appl. No.: 875,824

[22] Filed: Jun. 18, 1986

Related U.S. Application Data

[63] Continuation-in-part of Ser. No. 849,670, Apr. 9, 1986, which is a continuation-in-part of Ser. No. 671,850, Nov. 15, 1984, abandoned.

[30] Foreign Application Priority Data

Nov. 15, 1985 [EP] European Pat. Off. ........ 85308327.7

[51] Int. Cl.$^4$ .......................... A61K 9/00; A61L 15/03
[52] U.S. Cl. ........................ 424/449; 424/78; 424/80; 424/443; 424/444; 424/497; 514/509; 523/122; 524/569
[58] Field of Search ........................ 523/122; 524/569; 424/19, 28, 449, 497, 78, 80, 443, 444; 604/896, 897; 514/509

[56] References Cited

U.S. PATENT DOCUMENTS

| | | | |
|---|---|---|---|
| 1,624,089 | 4/1927 | Biddle | 523/122 |
| 2,286,636 | 6/1942 | Murray | 523/122 |
| 2,500,891 | 3/1950 | Alexander | 524/569 |
| 2,635,085 | 4/1953 | Gonnard et al. | 523/122 |
| 3,833,520 | 9/1974 | Tirpak et al. | 523/122 |
| 4,150,109 | 4/1979 | Dick et al. | 119/156 |
| 4,289,749 | 9/1981 | Keith et al. | 424/80 |
| 4,291,015 | 9/1981 | Keith et al. | 424/80 |
| 4,292,301 | 9/1981 | Keith et al. | 424/80 |
| 4,292,302 | 9/1981 | Keith et al. | 424/80 |
| 4,292,303 | 9/1981 | Keith et al. | 424/80 |
| 4,294,820 | 10/1981 | Keith et al. | 424/80 |
| 4,631,301 | 12/1986 | Kozuma et al. | 523/122 |
| 4,636,543 | 1/1987 | Helton | 524/569 |

FOREIGN PATENT DOCUMENTS

| | | | |
|---|---|---|---|
| 38-4677 | 4/1963 | Japan | 524/569 |
| 842492 | 7/1960 | United Kingdom | 524/569 |

*Primary Examiner*—Ronald W. Griffin
*Attorney, Agent, or Firm*—Sughrue, Mion, Zinn, Macpeak, and Seas

[57] ABSTRACT

A device for the controlled release and delivery of a pharmacologically active agent, comprising a vinyl gel layer and a pharmacologically active agent uniformly dispersed in the layer in a pharmacologically effective amount, the vinyl layer comprising a polyvinyl chloride resin, a primary plasticizer for the polyvinyl chloride resin, and an organic, nonvolatile gel forming additive in an amount sufficient to form a gel.

23 Claims, No Drawings

DEVICE FOR CONTROLLED RELEASE DRUG DELIVERY

CROSS REFERENCE TO RELATED APPLICATION

This application is a continuation-in-part application of our co-pending U.S. Application Ser. No. 06/849,670, filed Apr. 9, 1986, which is a continuation-in-part of our co-pending U.S. Application Ser. No. 06/671,850, filed Nov. 15, 1984, now abandoned.

BACKGROUND OF THE INVENTION

The present invention relates to a device for controlled release drug delivery, and more particularly to a polyvinyl chloride based controlled release drug delivery device.

In recent years, various drug delivery systems have been developed which provide substantial release of a drug, such as transdermal drug delivery systems. These systems have taken various forms. Thus, for example, it is known in the art to incorporate a drug in a gel by a batch technique. In this technique, a gel-forming composition containing the drug is poured into a tube and then heated to about 110° C. until it sets. The set gel is then sliced to provide individual product units. The prior art batch technique is slow and inefficient, and results in a product which is cosmetically inelegant and subject to syneresis where there is a leaking out of liquid from the gel. This batch technique also suffers from problems of reproducibility, difficulty in controlling the thickness of the product, and difficulty in slicing of the gel.

Another prior art transdermal delivery device has been provided in the form of a pouch containing a backing layer and a transmissive drug release rate controlling membrane, with a chamber therebetween which contains a solution or suspension of drug. If the pouch were to break, there would be an intermediate release of large amounts of drug, that is, there would be a "dumping" of drug.

It is known to prepare a pharmaceutical delivery device from a silicone liquid polymer which is mixed with the drug and then cured with a catalyst to form a biologically acceptable silicone polymer matrix having microsealed compartments throughout which contain the drug, which can be present in a hydrophilic solvent system. The biologically acceptable silicone polymer matrix can be placed in a sealed or unsealed biologically acceptable polymer container made of a material capable of forming thin walls or coatings through which pharmaceuticals can pass at a controlled rate. See, for example, U.S. Pat. Nos. 3,992,518, 3,946,106 and 4,053,580. If the drug is in powder form, large amounts of the drug cannot be employed because a stiff product results. Moreover, care must be taken to avoid poisoning of the catalyst, which can occur due to interactions between the catalyst and drug. For example, amine drugs when present in amounts of, for example, 25% by weight, kill the catalyst and therefore such drugs are not suitable for use in such amounts with silicone liquid polymers. The silicone liquid polymer operation is a costly batch type method which requires a proper mixing of the various ingredients, and it is time constrained once the ingredients are mixed together. The batch silicone liquid polymer method generally results in fixed size product units.

U.S. Pat. No. 4,336,243 discloses a microsealed transdermal nitroglycerin pad comprising a backing which is impervious to nitroglycerin absorption and transport, and a biologically acceptable silicone polymer matrix affixed thereto. The silicone polymer matrix is a cross-linked silicone rubber having microsealed compartments which are formed by in situ crosslinking of the silicone rubber after it is mixed with a hydrophilic solvent system containing the nitroglycerin and a hydrophobic solvent system which enhances nitroglycerin dispersion and transport. The hydrophobic solvent system can be comprised of isopropylpalmitate (IPP), mineral oil, cholesterol or a triglyceride of a saturated coconut oil acid or a mixture thereof. The combined hydrophilic and hydrophobic solvent systems which are incorporated within the matrix are stated to serve the unique purpose of partitioning and enhancing the diffusion of nitroglycerin throughout the matrix. The patent further discloses that a number of materials which are capable of forming thin walls or coatings through which pharmaceuticals can pass at a controlled rate can be used to form a biologically acceptable polymer container. Among the materials disclosed for this purpose is polyvinyl chloride, but no example of the use of polyvinyl chloride is shown in the patent. The polymers which are stated to be suitable for forming thin walls or coatings through which nitroglycerin can pass at a controlled rate are stated to have a durometer hardness of 30 to 100 Shore A, a tensile strength of 500 to 700 psi, an elongation of 100 to 400% and a tear strength of 70 to 100 ppi.

Canadian Pat. No. 930,668 discloses a bandage for administering drugs comprised of a backing member, a pressure sensitive adhesive, and at least one reservoir disposed between the backing member and pressure sensitive adhesive. The reservoir is comprised of a systemically active drug formulation confined within a wall member, the wall member being formed from a drug release rate controlling material. The reservoir can be in the form of discrete microcapsules or distinct reservoir compartments or layers. The reservoir can also be in the form of walled containers having one or more interior drug-containing chambers, as well as solid or gel matrixes having a systemically active drug distributed therethrough. The Canadian patent discloses a wide variety of materials which can be used to form the reservoir. Among the materials mentioned are silicone rubbers, hydrophilic polymers of monoesters of an olefinic acid, polyvinylalcohol, polyvinylacetate, plasticized polyvinylchloride, plasticized nylon, collagen, gelatin, and waxes such as polyethylene wax, oxidized polyethylene wax, hydrogenated castor oil and the like, with the silicone rubbers being preferred. The Canadian patent does not contain any examples showing the use of plasticized polyvinylchloride, and does not show the use of a PVC plastisol.

As is well known, polyvinyl chloride (PVC) is never used alone, but is always mixed with other ingredients before being processed. Polyvinyl chloride appeared at first to be an unpromising resin because it is insoluble in common solvents, cannot be molded without thermal decomposition and turns black in a few days exposure to sunlight. PVC, however, was discovered to form a rubberlike material when dissolved hot in high boiling solvents known as plasticizers and cooled to room temperature. PVC is now available in a number of different physical forms and types, and its manufacture depends on the form desired. Thus, PVC is available as a vinyl latex, a dispersion resin, or a general purpose resin.

PVC latexes are true colloidal dispersions of submicrometer particles in water, stabilized by a surfactant system, and need plasticizers in order to form a continuous film. The PVC in a vinyl latex is manufactured by emulsion polymerization.

Dispersion resins are produced by emulsion polymerization and are mixed with liquid plasticizers to form a colloidal dispersion of resin powder in plasticizer. Such dispersions are known as plastisols and are easily handled and readily pourable. On warming or on long standing at room temperature, the plastisol gels as the plasticizer solvates the resin, but the gel has little physical integrity. When a plastisol is heated to a temperature of about 148° to 177° C., the plastisol is transformed to a homogeneous melt which, upon cooling to below 50° C., results in a tough flexible product. The PVC resins made by emulsion polymerization are hard spheres of particle size between about 0.05 to 20 microns. They do not have the ability to absorb plasticizers. Therefore, a mixture containing, for example, 30% plasticizer and 70% PVC resin, produces a flowable liquid, known as plastisol. With certain plasticizers or resins, the plastisol may become a gelatinous mass under controlled conditions, and then may be used as a plastigel, for example, in the production of certain types of floor coverings.

It is also known to prepare transdermal delivery devices from polyvinyl chloride plastisol compositions, as disclosed in pending U.S. application Ser. No. 657,911, filed on Oct. 5, 1984 assigned to the same assignee as the present invention. Polyvinyl chloride generally is a stiff dry material which conforms poorly to the skin and delivers drug slowly.

General purpose PVC resins are made by mass and suspension polymerization processes, and comprise the largest amount of PVC resins, and are used chiefly to make so-called 100% vinyl products by a variety of molding and extrusion techniques. Resins intended for flexible applications should have good uptake of plasticizer in a dry blending operation and contain more than 25% of a plasticizer system. PVC compounds that contain less than 25% plasticizers are referred to as semi-rigid compounds. The PVC resins manufactured by suspension and bulk polymerization are 50 to 200 microns in diameter, such as 100 to 500 microns in diameter, and are like sponges. They are capable of absorbing large amounts of plasticizers, so that even a 50% plasticizer, 50% PVC resin composition would result in a non-flowing, solid material.

SUMMARY OF THE INVENTION

Accordingly, it is a primary object of the present invention to provide an improved device for the controlled release delivery of drugs.

Another object of the present invention is to produce such a device which can be manufactured by inexpensive techniques in high volume in a reproducible manner relatively quickly.

A further object of the present invention is to provide such a device which is flexible, which can be used with a wide variety of drugs, which has good release rates and which has good conformability to and feel to skin.

Additional objects and advantages of the present invention will be set forth in part in the description which follows and in part will be obvious from the description or can be learned by practice of the invention. The objects and advantages are achieved by means of the products, instrumentalities and combinations particularly pointed out in the appended claims.

To achieve the foregoing objects and in accordance with the present invention, there is provided a device for the controlled release of a pharmacologically active agent, comprising a gelled plasticized polyvinyl chloride layer and a pharmacologically active agent uniformly dispersed in the layer in a pharmacologically effective amount, the gelled plasticized polyvinyl chloride layer comprising a polyvinyl chloride resin, a primary plasticizer for the resin, and an organic, nonvolatile, gel forming additive in an amount sufficient to form a gel. The gel has a relatively low tensile strength, for example, a tensile strength of 500 psi or below, such as 350 psi or below. One especially preferred device has a tensile strength of below 150 psi, and preferably below 75 psi.

Preferably, based on the total weight of the vinyl gel layer, the resin is present in an amount of about 10 to about 75 weight percent and the primary plasticizer is present in an amount of about 20 to 85% weight.

The organic, nonvolatile, gel forming additive preferably is present in an amount of at least 5 weight percent, based on the total weight of the vinyl gel layer, more preferably is present in an amount of about 5 to about 30 weight percent, and still more preferably is present in an amount of 8 to 25% by weight.

As used herein, the total weight of the vinyl gel layer includes the weight of the pharmacologically active agent which is dispersed in the layer.

It is to be understood that both the foregoing general description and the following detailed description are exemplary and explanatory, but are not restrictive of the invention.

DETAILED DESCRIPTION OF THE PRESENT INVENTION

The device of the present invention comprises a gelled plasticized polyvinyl chloride layer and a pharmacologically active agent uniformly dispersed in the gel layer. The polyvinyl chloride gel in the present invention is prepared from polyvinyl resin, a primary plasticizer for the resin, and an organic, nonvolatile gel forming additive.

The polyvinyl chloride resin employed in the practice of the present invention can be any of the PVC resins which are known in the art and commercially available. The preferred grade of polyvinyl chloride resin employed in the practice of the present invention is that which is specifically used in preparing PVC plastisols, namely, PVC resins which are made by the well known emulsion polymerization process, which are hard spheres of particle size between 0.05 and 20 microns, such as between 1 and 20 microns, for example, between 1 and 5 microns, or between 0.05 and 1 micron, and which do not have the ability to absorb plasticizers to any great extent. Instead, the plasticizer wets the resin particles at room temperature and only then very slowly penetrates and solvates the resin. These PVC resins when mixed with plasticizers, such as a mixture of 30% primary plasticizer, 70% PVC resin, give a flowable liquid known as plastisol which can then be fused at, for example, approximately 250° F. for approximately 30 seconds to provide a solid polymer layer.

The PVC resin employed in the present invention for preparation of the gelled vinyl layer can also be a general purpose PVC resin which is produced by suspension or bulk (mass) polymerization. When a general purpose grade of PVC resin is used, it is mixed with the other components of the present invention in the presence of a mutual solvent (e.g. cyclohexanone, methyl ethyl ketone, chloroform, ethyl acetate, etc.) to form a solution having a castable viscosity ($\approx$10,000 to 25,000 centipoises). For example, the solvent can comprise about 40 to about 70% by weight of the solution formed by mixing the solvent with the other components. The solution, thus prepared, can be cast onto a desired substrate, such as a backing layer, and subsequently dried in an air circulating oven at 70° to 125° C. until the solvent is volatilized to form the gelled vinyl layer. Generally, this drying can be accomplished in about 2 to 5 minutes. The general purpose resins are used in calendering and extrusion processes, and such processes can be employed to prepare the gelled vinyl layer of the present invention. When using calendaring or extrusion processes, care must be taken to avoid damaging the drug by the heat encountered in these processes. A gelled layer in accordance with the present invention can also be prepared from an organosol which, as is well known, is a plastisol which is diluted with a volatile solvent that evaporates during the heating process.

The molecular weight of the PVC resins employed in the present invention preferably is a weight average molecular weight between 80,000 and 250,000, such as a weight average molecular weight of 123,000. A suitable polyvinyl chloride resin is one sold by Occidental Chemical Co. under the designation FPC 6338. The polyvinyl chloride resin can be a copolymer containing preferably at least 90% by weight vinyl chloride monomer units, such as a copolymer based on vinyl chloride and vinyl acetate.

The polyvinyl chloride resin generally is present in the layer in an amount of 10 to 75 weight percent, preferably 20 to 65 weight percent, and still more preferably 25 to 50 weight percent, based on the total weight of the vinyl gel layer.

The primary plasticizer which is employed in the present invention can be dioctylphthalate (DOP), benzylbutylphthalate, tri-2-ethylhexylmalaete, dioctyl adipate, epoxidized soybean oil, polymeric adipate plasticizers, which are polymers of adipic acid with a monomer, such as propylene glycol, and for example, can be obtained under the designation Drapex 334F from Witco Chemical Corp., or any other known primary plasticizer for PVC which is biologically acceptable. Mixtures of known plasticizers can be used. The term "primary plasticizer" as used herein refers to a plasticizer which can be used alone to effect plasticization and is highly compatible with PVC at high concentrations, such as, for example, 150 parts per hundred. Primary plasticizers are contrasted with "secondary plasticizers" which, because of limited compatibility with PVC, cannot be used alone. See, Kirk-Othmer Encyclopedia of Chemical Technology, Volume 23, 3rd Edition, especially pages 913 and 914 for a discussion of primary and secondary plasticizers.

The primary plasticizer generally is present in an amount of 20 to 85 weight percent, preferably 20 to 60, based on the total weight of the vinyl gel layer.

The vinyl layer of the present invention further contains an organic nonvolatile gel forming additive in an amount sufficient to provide a gel. As used herein with reference to the present invention, the provision of a gel refers to the formation of a film layer that is characterized by an opaque coloration or appearance and a relatively low tensile strength of, for example, of about 500 psi or below such as 350 psi or below. The gel can have a tensile strength of no more than 150 psi, such as less than 75 psi. The gel preferably has a low elongation at break of, for example, less than 25%, and a low tear strength of, for example, less than 30 lbs/inch. In one especially preferred embodiment of the present invention, the gel layer at 18 mil thick has a tensile strength below 50 psi, an elongation at break below 10% and a tear strength below 20 lbs/inch. The gel layer, of course, has sufficient strength to maintain its integrity in normal use. The above properties are determined in a standard Scott tensile tester at room temperature employing standard procedures. The amount of gel forming additive generally is at least 5% by weight of the gel layer, preferably from 5 to 30% and still more preferably 8 to 25%.

As discussed above, compositions of emulsion polymerized PVC and primary plasticizer are pourable dispersions of resin powder and plasticizers, and are called plastisols. On heating to high temperature, they fuse and become clear, and upon cooling, form a clear fused structure of high tensile strength. In accordance with the present invention, the addition of the nonvolatile gel forming additive to the composition which is being processed, such as the liquid plastisol composition or the casting solution, and after heating to a high temperature and cooling, results in the formation of a white or opaque gel structure of much lower tensile strength as compared to the clear fused structure formed by the same composition (such as a plastisol composition) which does not contain the gel forming additive. While it is known that certain palmitate esters can plasticize PVC to a limited extent, and that these esters are compatible with PVC at concentrations less than 10% by weight, as disclosed in Sears, J. K. and Darby, J. R., *The Technology of Plasticizers,* John Wiley and Sons, New York, 1982, it is surprising that PVC mixtures, such as PVC plastisol mixtures, containing a sufficient amount of gel forming additive such as 10% or more, exhibit greater losses in tensile strength than from the addition of equivalent amounts of primary plasticizers.

The compositions of the present invention form an intact structural device which can still hold large quantities of drugs and form a soft gel structure. These devices are excellent for transdermal drug delivery because the devices are soft and make good skin contact, the drug readily diffuses from the device, and the device can contain large quantities of drug.

It is known in the prior art to form a gel by adding certain metallic soap compounds, such as aluminum stearate, to a polyvinyl chloride resin plastisol. These compounds are poorly soluble in the plastisol and to the extent they are soluble, are soluble only at low levels such as 1 or 2 weight percent. The moment these compounds are added to the plastisol, there is the formation of a thick gel structure. This gel structure is non-processable and when heated or left to stand forms a clear, hard polyvinyl chloride system having high tensile strength.

It is also known that vinyl plasticizer compositions first imbibe plasticizer, swell, and upon heating, a gel forms at certain temperatures. The temperature at which there is gel formation is known as the gel point. If heating is continued, a uniform solution is obtained in which the vinyl material becomes clear. The temperature at which a plastisol becomes clear is known as the clear point, at which point there is obtained a completely fused structure. The gel formation, which occurs at the gel point and higher temperature, however, is not stable in that the physical properties and release properties of such a gel change with time so that the drug release rates from such a gel are not reproducible and cannot be controlled. With the passage of time, the tensile strength of such a gel increases and the drug release slows down. By adding a gel forming additive, however, it has been found that a very stable gel is formed when the composition is heated to a temperature between the gel point and the clear point, and then cooled. In the present invention, in the case of solution casting, gel formation will occur upon evaporation of the solvent. In the case of extrusion and calendering, the material will be processed as a gel or a solution depending on the solubility of the gel forming additive in the formulation mixture at the processing temperatures, and in any event, upon cooling a stable gel form results. The stable gel of the present invention has physical properties (for example, tensile strength) and release properties that do not change with time and provides controlled and consistent release rates which can be reproduced. The gel formed in the present invention is characterized by an opaque coloration and low tensile strength. Fused vinyl compositions are generally stiff and do not provide good contact with the skin, but the gel layer of the present invention is a relatively weak, highly flexible and soft material and provides good contact with skin and a conformable patch. The gel of the present invention does not exhibit syneresis and is an incompletely fused composition, as evidenced by its opaque color or appearance and low tensile strength, which indicates that the gel layer has an open structure which enables it to release vastly more drug. It has been found that the dissolution rate of a drug increases as the tensile strength decreases in the device of the present invention.

The gel forming additive generally is a compound which has a limited compatibility or partial compatibility with the PVC resin and with the PVC resin/primary plasticizers system. By limited compatibility it is meant that the gel forming additive will form a single phase when added at certain concentrations, but that as the amount of gel forming additive increase, there comes a point at which a second liquid phase is formed. Compounds known as secondary plasticizers generally meet this requirement and can be used as the gel forming additive.

The gel forming additive generally is a non-volatile compound so that during processing, that is, during formation into a film by heating, less than about 5%, preferably less than about 2%, of its weight is lost by evaporation. If gel forming additives are employed which have too great a volatility, difficulty is experienced during processing in obtaining reproducible films.

The gel forming additive which is employed in the present invention can be, for example, at least one ingredient selected from isopropyl palmitate (IPP), isopropyl myristate (IPM), soybean oil (unepoxidized), castor oil, linseed oil, olive oil, mineral oil, petrolatum (otherwise known as petroleum jelly or paraffin jelly and which preferably is employed with a processing aid such as cetyl alcohol), a triglyceride such as a mixture of caprylic and capric triglycerides, and non-ionic surfactants. The non-ionic surfactants preferably are the non-ionic ethoxylated surfactants, such as those sold under the tradename Span or Tween, for example, Tween 20 (polyoxyethylene [20] sorbitan monolaurate).

In the present invention, the gel forming additive preferably is added to the plastisol in an amount which is up to or just below its limit of compatibility in the plastisol so that there is no formation of a second phase. The plastisol composition is then heated to a temperature above the gel point, but below the clear point to bring about gel formation. If the amount of gel forming additive added to the plastisol is too low, a stable gel will not form, but rather, the composition will be transformed into a clear, hard, fused polyvinyl chloride resin. If too great an amount of gel forming additive is employed, an undesired second phase will form. Similarly, in the case of solution casting, extrusion or calendaring, the amount of gel forming additive is controlled to avoid the formation of an undesired second phase during processing and to avoid formation of a clear, hard fused polyvinyl chloride resin.

The vinyl gel film of the present invention exhibits properties of typical gels in that liquid oozes out when the gel is placed under pressure, and diffusion in the film is as fast as it would be in a liquid. Microscopically, there is a network structure, with the continuous phase most likely being that of polymer rather than liquid.

Preferably, when the gel forming additive is either IPP or IPM, 15 to 25 wt. percent, such as 20 wt. % of gel forming additive is used with a drug in solid form, and 5 to 15 wt. percent, such as 10 wt. %, is used with a drug in liquid form. When the gel forming additive is a mineral oil, preferably 15 to 25 wt. percent of gel forming additive is employed. Petrolatum is preferably employed in amounts of 10 to 20 wt. percent, and silicone oil is preferably employed in amounts of 10 to 25 wt. percent.

A wide variety of pharmacologically active agents or drugs can be incorporated in the gel of the present invention. For example, nitroglycerin, phenylpropanolamine hydrochloride, timolol, albuterol, isosorbine dinitrate, guanfacine, nadolol, clonidine, or prostaglandins are examples of suitable drugs than can be employed. The drugs can be, for example, beta-blockers, antiasthmatics, i.e., bronchodilators, antihypertensive or antianginal agents. Examples of other suitable pharmacologically active agents which can be used are described in the above noted U.S. Pat. No. 3,946,106 and Canadian Pat. No. 930,668, which are hereby incorporated by reference.

The amount of drug incorporated in the drug delivery device varies depending on the particular drug, the desired therapeutic effect, and the time span for which the device provides therapy. Since a variety of devices in a variety of sizes and shapes are intended to provide the dosage regimens for therapy for a variety of maladies, there is no critical upper limit in the amount of drug incorporated in the device. The lower limit, too, will depend on the activity of the drug, and the time span of its release from the device. Thus, it is not practical to define a range for the therapeutically effective amount of drug to be incorporated in or released by the device. It is noted, however, that the amount of drug incorporated into the "gel" layer can be as low as 0.1 wt. percent, or as high as 50 wt. percent, based on the total weight of the drug and gel layer. For example, amounts of 5 to 10% or 20 to 40% of drug can be incorporated into the gel layer. The drug can be in liquid or powder form, and large amounts of drug can be employed, even when the drug is in powder form.

The compositions employed in the present invention can contain suitable amounts of other ingredients such as processing aids, stabilizers, cosmetic enhancement aids, skin penetration enhancement aids and the like. Generally, the total amount of these other ingredients when present is no more than 30 to 40 wt. percent of the total weight of the vinyl gel layer. Processing aids and stabilizers generally would be used in low amounts of, for example, 5 wt. percent or less, such as 1 to 3 wt. percent for each of such ingredient which is present.

An especially preferred vinyl gel layer in accordance with the present invention contains 5 to 25 wt%, for example 8 to 25, such as 10 to 20 wt% nitroglycerin, 30 to 60 wt% PVC, preferably 30 to 50 wt% PVC, and more preferably about 40 to 48 wt% PVC, 25 to 50 wt% of a primary plasticizer, such as DOP, and more preferably 25 to 40 wt% of a primary plasticizer, 5 to 20 wt%, for example, 5 to 15 wt% or 10 to 20 wt% of a gel forming additive, such as IPP, and 0 to 3 wt% of a material which aids in controlling viscosity, such as aerosil.

The vinyl layer of the present invention is inert and there is no danger of poisoning of catalyst inasmuch as no catalysts are used and there is no danger of adverse reactions with the drugs since no chemical reactions occur. The gel layer can be manufactured quickly, in an inexpensive manner, with high volume, in a reproducible manner and the process is flexible to give any desired shape and thickness to the vinyl gel layer. The gel layer is a drug release rate controlling material which continuously meters the flow of drug to the skin or mucosa at a controlled and predetermined rate over a prolonged period of time. The rate is controlled by the thickness of the gel layer and its composition and is a function of the nature of the particular drug incorporated therein.

In practicing the present invention, the PVC, primary plasticizer, and gel forming additive are first blended to form a plastisol, the drug is then incorporated into the blended plastisol, and the blended plastisol is then formed into a gelled plastisol layer, which is the vinyl gel layer of the present invention. The blended plastisol preferably is stirred immediately before processing into the gel film to insure that no second phase is formed. Formation into the gelled layer can occur by coating the blended, liquid plastisol onto a suitable substrate and then heating the liquid plastisol for short periods, such as 15 to 60 seconds, preferably 15 to 30 seconds, at a temperature of, for example 220° to 350° and preferably 250° to 280° F. The heating can take place by allowing the coated substrate to pass through an oven or go around a heated drum. The use of a plastisol composition to form the gelled layer enables the layer to be formed by using a low temperature for a short period of time and provides conditions which do not effect the stability of the drug.

The gel layer of the present invention can be provided in a device which contains a backing layer, the gel layer, and means to secure the device to a patient's skin or mucosa. The backing substantially blocks loss of drug from the gel layer other than in the direction of the surface which in use will contact the patient's skin. The substrate onto which the blended plastisol or the castable solution can be coated can be used as a backing layer for the device. The backing can be a single layer of drug impermeable plastic or other material, or can be comprised of two or more layers. The backing substantially blocks loss of drug from the gel layer other than in the direction of the surface which, in use, will contact the patient's skin. Suitable backing materials include, for example, polyethylene terephthalate, polyethylene, aluminum foil and the like. The backing layer can have a thickness of, for example, 0.5 to 5 mils, such as 0.5 mils, and the gel layer can have a thickness of, for example, 0.5 to 50 mils, such as about 4 mil.

The means to secure the device to a patient's skin or mucosa preferably is a pressure sensitive adhesive strip containing a pressure sensitive layer and a non-adhesive layer formed from a plastic. The pressure sensitive adhesive layer can be applied to the surface of the backing layer which does not contact the gel layer and can extend past the edges of the backing layer and gel layer to form a border area which adhesively attaches to the skin or mucosa. A typical device can be provided with an active surface areas of the gel of, for example, 1 inch by 1 inch, with the adhesive layer providing a border which is 1 to 1½ inches wide. When not in use, the entire surface intended for skin contact is preferably covered with a release liner or the like which is removed to expose surfaces of the adhesive layer and drug containing gel layer for application to the patient's skin.

An alternate means to secure the device can comprise a pressure sensitive layer which is applied directly to the active face of the vinyl gel (e.g. plastic) layer. In this embodiment of the invention, the drug would then pass through the pressure sensitive layer before contacting the patient's skin.

It is also possible in accordance with the present invention to apply a rate controlling membrane on top of the gelled vinyl layer. The rate controlling membrane would contact the patient's skin or mucosa and further control the rate of application of the drug to the patient. A suitable rate controlling membrane is one which is made from an ethylene-methyl acrylate copolymer having a methyl acrylate content ranging from 2 to 90 wt% of methyl acrylate monomer units. The rate controlling membrane can be applied, for example, in a thickness of from 1 to 5 mils.

The following examples are given by way of illustration to further explain the principles of the invention. These examples are merely illustrative and are not to be understood as limiting the scope and underlying principles of the invention in any way. All percentages referred to herein are by weight unless otherwise indicated.

In each of the following examples, the PVC resin which was employed was one sold under the description FPC 6338 by Occidental Chemical Corp. and having a particle size between 1 and 5 microns.

EXAMPLE 1

This example illustrates the effect of the addition of IPP to a PVC/DOP plastisol in which the PVC to DOP ratio is maintained at 3:2. The PVC, DOP and IPP were blended together to form a plastisol. The plastisol was formed into a thin film having a thickness of 18 mil by heating at a temperature of 290° F. for 60 seconds and cooling to room temperature. The results are shown in Table 1 below.

TABLE 1

| IPP Content (% w/w) (weight of IPP/total weight of PVC, DOP, IPP) | Coloration | Does it break by Scratching With a Fingernail? |
|---|---|---|
| 0 | Clear | No |
| 5 | Translucent | No |
| 10 | Opaque | Yes |
| 15 | Opaque | Yes |

TABLE 1-continued

| IPP Content (% w/w) (weight of IPP/total weight of PVC, DOP, IPP) | Coloration | Does it break by Scratching With a Fingernail? |
|---|---|---|
| 20 | Opaque | Yes |
| 25 | Opaque | Yes |

As can be seen from the above Table, at 10% IPP and above, the PVC structure is no longer clear but is white or opaque, and is capable of being broken with a fingernail indicating that it has low tensile strength.

EXAMPLE 2

This example illustrates the effect of the addition of IPP to a PVC device containing 10% nitroglycerin (GTN). Three formulations were prepared. The first formulation, formulation A, containing 30% DOP without IPP. The second formulation, formulation B, contained 42% DOP without IPP. The third formulation, formulation C, was prepared in accordance with the present invention and containing 10% IPP and 32% DOP. The formulations were formed into thin films, having a thickness of 18 mils by heating the formulation at a temperature of 290° F. for 60 seconds and then cooling to room temperature. Two samples of each formulation were tested, and the various formulations and results for tensile testing, break elongation, and durometer hardness are set forth in Table 2 below for the two samples.

TABLE 2

| Formulation | Tensile Testing PSI | Break Elongation (%) | Durometer (Shore A) |
|---|---|---|---|
| A. | | | |
| (a) 10% GTN | | | |
| (b) 58% PVC | | | |
| (c) 30% DOP | 260 | 50 | 77 |
| (d) 2% Aerosil | 310 | 69 | 77 |
| B. | | | |
| (a) 10% GTN | | | |
| (b) 46% PVC | | | |
| (c) 42% DOP | 173 | 94 | 54 |
| (d) 2% Aerosil | 140 | 73 | 57 |
| C. | | | |
| (a) 10% GTN | | | |
| (b) 46% PVC | | | |
| (c) 32% DOP | ** | ** | 55 |
| (d) 2% Aerosil | ** | ** | 57 |
| (e) 10% IPP | | | |

**These samples break as soon as the jaws of the tester are closed. The force to stretch and the elongation at breaking are well below the limits of the instrument of 50 PSI and 10%, respectively.

As can be seen from the Table, when the IPP was added, the tensile strength and break elongation of the plastisol was significantly lower than the formulations which did not contain IPP, and were below 50 psi and 10%, respectively.

EXAMPLE 3

Formulations were prepared in which the ratios of PVC to dioctylphthalate (DOP) were varied, at three concentrations of IPP. The formulations were formed into thin films of a thickness of 18 mil by heating them at a temperature of 290° F. for 60 seconds and cooling to room temperature. The films were studied for tensile strength with a Scott tester. The results are shown in Table 3 below.

TABLE 3

| PVC:DOP Weight Ratio | Weight % IPP | Tensile Break, in PSI |
|---|---|---|
| 1.0 | 0% | 324 |
| 1.5 | 0% | 504 |
| 1.0 | 20% | 195 |
| 1.2 | 20% | 189 |
| 1.5 | 20% | 192 |
| 1.0 | 30% | 12 |
| 1.2 | 30% | 19 |
| 1.5 | 30% | 28 |

As can be seen in Table 3, the tensile strength decreased with increasing IPP content. At 0% IPP, there was no gel formation, and a high tensile strength. At 20% IPP, although the tensile strength declined, there was no gel formation because the amount of IPP used was still in the range of compatability. At 30% IPP, the amount of IPP was near its compatibility limit, the tensile strength decreased drastically and there was gel formation. The decrease in tensile strength far exceeded the decrease observed for an equivalent amount of additional DOP.

EXAMPLE 4

This example illustrates the improved release rates that can be obtained by forming a vinyl gel layer in accordance with the present invention. Four formulations containing nitroglycerin were prepared and formed into thin films of 36.5 mil thickness by heating them at a temperature of 259° F. for 20 seconds and cooling to room temperature. A patch was cut from each film and subjected to a standard U.S.P. dissolution paddle test in water at 37° C. The percent nitroglycerin released in three hours into dissolution was determined. The first formulation (Formulation A) did not contain any gel forming additives, whereas the three other formulations were prepared in accordance with the present invention and were formed into gels by the addition of various gel forming additives. The various formulations and results obtained are shown below.

Control Formulation A
  54% PVC
  36% DOP
  10% Nitroglycerin
Dissolution of nitroglycerin after three hours was 13.8 weight percent.

Formulation B
  43% PVC
  29% DOP
  20% Tween 20
  8% Nitroglycerin
Dissolution of nitroglycerin after three hours was 24.2 weight percent.

Formulation C
  43% PVC
  29% DOP
  19% IPP
  1% Aerosil
  8% Nitroglycerin
Dissolution of nitroglycerin after three hours was 48.9 weight percent.

Formulation D
  43% PVC
  29% DOP
  20% Triglycerides (Miglyol H-12, neutral oil, a mixture of caprylic and capric triglycerides)

8% Nitroglycerin

Dissolution of nitroglycerin after three hours was 37.2 weight percent.

EXAMPLE 5

This example illustrates differences in transport of the drug prostaglandin across the human epidermis at 31° C. The prostaglandin was obtained from Lederle Labs under designation CL-115347, and was formulated into four formulations which were formed into thin films of a thickness of 38 mils by heating at 280° F. at 30 seconds. Equal sized patches were then cut from each film and tested for transport. Formulation A was a control formulation whereas formulations B, C and D were formed into gels in accordance with the present invention. The composition of each formulation and the results of the transport tests are set forth below.

Control Formulation A
  64% PVC
  34% Dioctyl adipate
  2% Prostaglandin

The flux across the skin was 0.17±0.04 micrograms/sq.cm./hr.

Formulation B
  43% PVC
  34% Dioctyl adipate
  2% Prostaglandin
  20% DC 556 silicone oil obtained from Dow Corning
  1% Aerosil The flux across the skin was 0.43±0.04 micrograms/sq.cm./hr.

Formulation C
  43% PVC
  34% Dioctyl adipate
  2% Prostaglandin
  20% DC 190 silcone oil obtained from Dow Corning
  1% Aerosil The flux across the skin was 0.4±0.1 micrograms/sq.cm./hr.

Formulation D
  49% PVC
  27% Dioctyl adipate
  2% Prostaglandin
  2% Cetyl alcohol (thickener to improve viscosity and processing)
  20% Petrolatum The flux across the skin was 0.8±0.1 micrograms/sq.cm./hr.

EXAMPLE 6

This example illustrates differences in transport of the drug nadalol across human epidermis at 31° C. The drug was formulated into the following three formulations which were formed into thin films having a thickness of 20 mil by heating at 290° F. for 30 seconds.

Formulation A
  30% Nadolol
  4% Propylene glycol
  16% Isopropyl myristate (IPM)
  30% PVC
  20% Dioctyl adipate Formulation A formed a gel film in accordance with the present invention and the flux across the skin was 1.2 milligrams/sq.cm./day.

Formulation B
  30% Nadolol
  4% Propylene glycol
  6% Isopropyl myristate
  20% PVC
  18% Dioctyl adipate
  2% Aerosil The film formed by formulation B was not a gel, it was not opaque, and did not break when subjected to the finger scratch test. The flux across the skin was 0.08 milligram/sq.cm./day.

Formulation C
  30% Nadolol
  20% Isopropyl myristate
  30% PVC
  20% Dioctyl adipate Formulation C formed a gel film in accordance with the present invention and the flux across the skin was 0.8±0.08 milligram/sq.cm./day.

EXAMPLE 7

Three 18 mil polyvinylchloride films were prepared in accordance with the present invention containing either (1) 20% mineral oil, or (2) 20% DC556 silicone oil, or (3) 18% petrolatum plus 2% cetyl alcohol (L352-1). The resin: dioctyl phthalate ratio was 3:2. Each of these films was opaque, had a tensile strength, elongation at break and tear strength below 75 psi, 25%, and 30 lbs/inch, respectively. The films were prepared by heating at 290° F. for 60 seconds.

EXAMPLE 8

A thin film polyvinylchloride gel was prepared in accordance with the present invention containing 30 wt% nicotine as drug, 25 wt% Admex 760 as primary plasticizer, 5 wt% isopropyl myristate (IPM) as gel forming additive and 39 wt% of PVC resin. The film had a tensile strength of 240 psi. Amdex 760 is a linear polyester plasticizer, sold by Sherax Chemical Co., Inc. (Nuodex, Inc.) Dublin, Ohio, having a high molecular weight, and is a permanent primary plasticizer which is practically non-migrating and non-extractable.

It will be understood that the above description of the present invention is susceptible to various modifications, changes, adaptations, and the same are intended to be comprehended within the meaning and range of equivalents of the appended claims.

What is claimed is:

1. A device for the controlled release and delivery of pharmacologically active agent, comprising a gelled vinyl layer and a pharmacologically active agent uniformly dispersed in the layer in a pharmacologically effective amount, said gelled vinyl layer comprising a polyvinyl chloride resin, a primary plasticizer for the polyvinyl chloride resin, and an organic, nonvolatile gel forming additive in an amount sufficient to form a gel.

2. The device according to claim 1, wherein the resin is present in an amount of 10 to 75 weight percent and the primary plasticizer is present in an amount of 20 to 85 weight percent, based on the total weight of the vinyl gel layer.

3. A device as in claim 2, wherein the gel forming additive is present in an amount of from 5 to 30% by weight, based on the total weight of the vinyl gel layer.

4. A device as claimed in claim 3, wherein the pharmacologically active agent is present in an amount of 0.1% to 50% by weight, based on the total weight of the vinyl gel layer.

5. A device as in claim 1, wherein the polyvinyl chloride resin is present in an amount of from 20 to 65%, the primary plasticizer is present in an amount of from 20 to 60% by weight, the gel forming additive is present in an amount of from about 8 to 25%, and the pharmacologically active agent is present in an amount of from 0.1% to 50% by weight, based on the total weight of the vinyl gel layer.

6. A device as claimed in claim 1, wherein the gel forming additive is at least one ingredient selected from isopropylpalmitate, isopropyl myristate, mineral oil, silicone oil, unepoxidized soybean oil, castor oil, linseed oil, olive oil, or petrolatum.

7. A device as claimed in claim 1, wherein the gel forming additive is a non-ionic surfactant or a triglyceride.

8. A device as in claim 1, wherein said primary plasticizer is dioctyl phthalate, a polymeric adipate plasticizer, epoxidized soybean oil or dioctyl adipate.

9. A device as in claim 1, wherein the pharmacologically active agent is nitroglycerin, timolol, albuterol, isosorbide dinitrate, clonidine, guanfacine, nadolol or prostaglandin.

10. The device according to claim 1, wherein the gel layer is opaque, has a tensile strength below 50 psi, a break elongation below 10% and a tear strength below 20 lbs/inch.

11. The device according to claim 1, including a backing layer on one side of the gel layer.

12. A device as claimed in claim 1, wherein the drug is in solid form and the gel forming additive is isopropyl palmitate or isopropyl myristate present in an amount of 15 to 25 weight percent based on the weight of the vinyl gel layer.

13. A device as claimed in claim 1, wherein the drug is in liquid form and the gel forming additive is isopropyl palmitate or isopropyl myristate present in an amount of 5 to 15 weight percent based on the weight of the vinyl gel layer.

14. A device as claimed in claim 1, wherein the gel forming additive is mineral oil present in an amount of 15 to 25 weight percent, based on the weight of the vinyl gel layer.

15. A device as claimed in claim 1, wherein the gel forming additive is silicone oil present in an amount of 10 to 25 weight percent, based on the weight of the vinyl gel layer.

16. The device according to claim 1, wherein the gel has a tensile strength of 500 psi or below.

17. The device according to claim 16, wherein the gel has a tensile strength below 350 psi.

18. The device according to claim 16, wherein the gel has a tensile strength below 150 psi.

19. The device according to claim 16, wherein the gel has a tensile strength below 75 psi.

20. The device according to claim 1, comprising about 5 to 25 weight percent nitroglycerin, about 30 to 50 weight percent PVC, about 25 to 50 weight percent of primary plasticizer, and about 5 to 20% of gel forming additive.

21. The device according to claim 20, wherein the primary plasticizer is dioctyl adipate and the gel forming additive is isopropyl palmitate.

22. The device according to claim 1, wherein the polyvinyl resin is a suspension polymerized resin.

23. The device according to claim 1, wherein the polyvinyl resin is a bulk polymerized resin.

* * * * *